(12) United States Patent
Frey et al.

(10) Patent No.: US 9,995,703 B2
(45) Date of Patent: Jun. 12, 2018

(54) DEVICE SIMILAR TO ELECTROCHEMICAL CAMERA AND METHOD FOR PRODUCING DEVICE

(75) Inventors: Alexander Frey, München (DE); Walter Gumbrecht, Herzogenaurach (DE); Peter Paulicka, Erlangen (DE); Meinrad Schienle, Ottobrunn (DE); Manfred Stanzel, Erlangen (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 1325 days.

(21) Appl. No.: 13/262,578

(22) PCT Filed: Mar. 2, 2010

(86) PCT No.: PCT/EP2010/052616
§ 371 (c)(1),
(2), (4) Date: Nov. 16, 2011

(87) PCT Pub. No.: WO2010/112287
PCT Pub. Date: Oct. 7, 2010

(65) Prior Publication Data
US 2012/0108456 A1   May 3, 2012

(30) Foreign Application Priority Data
Mar. 31, 2009 (DE) .................. 10 2009 015 114

(51) Int. Cl.
| C40B 60/00 | (2006.01) |
| C40B 60/12 | (2006.01) |
| G01N 27/327 | (2006.01) |
| G01N 33/543 | (2006.01) |
| C40B 30/04 | (2006.01) |
| C40B 50/18 | (2006.01) |

(52) U.S. Cl.
CPC ..... G01N 27/3277 (2013.01); G01N 33/5438 (2013.01)

(58) Field of Classification Search
CPC .................................................. C40B 30/04
USPC ............................................................ 506/9
See application file for complete search history.

(56) References Cited

U.S. PATENT DOCUMENTS

| 5,605,662 A | 2/1997 | Heller et al. |
| 6,872,531 B2 | 3/2005 | Hosoi |
| 7,713,748 B2 * | 5/2010 | Wei ...................... G01N 33/558 422/401 |
| 2003/0068639 A1 | 4/2003 | Haneder et al. |
| 2003/0113528 A1 | 6/2003 | Moya |
| 2006/0137984 A1 | 6/2006 | Gumbrecht et al. |
| 2006/0141469 A1 * | 6/2006 | Rossier ............ B01L 3/502707 435/6.11 |
| 2006/0172340 A1 * | 8/2006 | Wohlstadter ........... G01N 21/66 435/7.1 |
| 2006/0252047 A1 | 11/2006 | Ekstrom et al. |
| 2008/0132429 A1 | 6/2008 | Perov et al. |
| 2008/0199974 A1 * | 8/2008 | Frey ................... G01N 27/3277 438/1 |
| 2009/0069198 A1 * | 3/2009 | Havens et al. .................. 506/32 |

FOREIGN PATENT DOCUMENTS

| CN | 1462878 | 12/2003 |
| DE | 102 59 821 A1 | 8/2004 |
| DE | 102004019357 A1 | 11/2005 |
| DE | 101 42 691 B4 | 4/2006 |
| EP | 1 258 287 A2 | 11/2002 |
| JP | 11-502617 | 3/1999 |
| JP | 2006-510882 | 3/2006 |
| JP | 2007-212215 | 8/2007 |
| WO | 00/62047 | 10/2000 |
| WO | 03/012442 A2 | 2/2003 |
| WO | WO-2004010143 A2 * | 1/2004 ........... G01N 33/525 |
| WO | 2005/008244 A1 | 1/2005 |
| WO | 2008/068678 A1 | 6/2008 |

OTHER PUBLICATIONS 102009015114.1, Mar. 31, 2009, Frey et al., Siemens Aktiengesellschaft.
German Office Action for Application No. 102009015114.1-52; dated Apr. 28, 2010.
International Search Report for Application No. PCT/EP2010/052616; dated May 27, 2010.
Application No. 102009015114.1, filed Mar. 31, 2009, Frey et al., Siemens Aktiengesellschaft.

* cited by examiner

Primary Examiner — Amy M Bunker
(74) Attorney, Agent, or Firm — David S. Safran

(57) ABSTRACT

A device for detecting chemical or biochemical substances in fluids for use in an electrochemical camera. The device includes a first carrier having a sensor array with a plurality of electrochemical sensors. A second carrier includes a porous layer having at least one functional region, in which specifically binding capturing molecules are immobilized. The at least one functional region is arranged directly adjacent to at least one non-functionalized region. Assigned to the at least one functional region and the at least one non-functionalized region are several sensors of the sensor array, for use as the electrochemical camera.

19 Claims, 3 Drawing Sheets

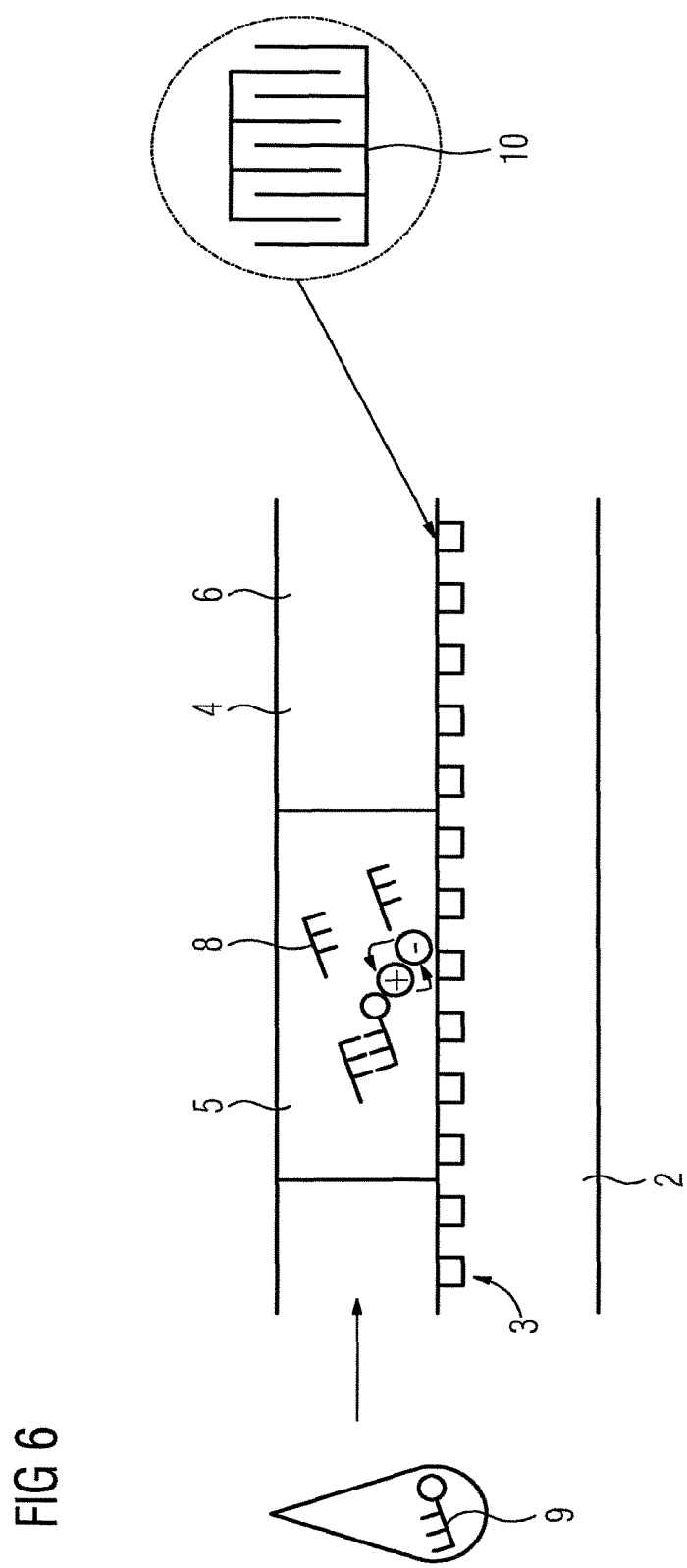

DEVICE SIMILAR TO ELECTROCHEMICAL CAMERA AND METHOD FOR PRODUCING DEVICE

CROSS REFERENCE TO RELATED APPLICATIONS

This application is the U.S. national stage of International Application No. PCT/EP2010/052616, filed Mar. 2, 2010 and claims the benefit thereof. The International Application claims the benefits of German Application No. 102009015114.1 filed on Mar. 31, 2009, both applications are incorporated by reference herein in their entirety.

BACKGROUND

Described below is a device similar to an electrochemical camera for detecting chemical or biochemical substances in liquids, a method for producing the device and the use thereof.

The detection of substances in liquids is gaining more and more in importance both in chemistry and in biochemistry. In this case, use is increasingly being made of electrochemical sensors which, for space reasons, are arranged on a carrier in the form of an array. Possible materials for the carriers are semiconductor materials such as, for example, silicon Si, germanium Ge or gallium arsenide GaAs. When these materials are used, semiconductor technology enables the integration of circuits for signal processing and evaluation of the signals of the electrochemical sensors on the same carrier on which the sensor array is situated.

Since the carrier material Si, Ge or GaAs is expensive and complicated to produce, attempts are made to form structures such as sensors, for example, as small as possible. In this case, care should be taken to ensure reliable functioning. In general, a sensor has finger-shaped interdigital electrodes, having an extremely small structure width in the range of micrometers. Inter alia, gold, platinum, silver-silver chloride or other metals are appropriate as electrode materials. The sensors are arranged regularly on the surface of the carrier, at distances from one another in the range of from a hundred nanometers to several millimeters.

In order to be able to detect chemical or biochemical substances in a liquid electrochemically, the electrodes are coated with molecules which interact with the substances. The interaction is directly or indirectly electrochemically detected. Different sensors are coated with different molecules, such that different chemical or biochemical substances can be detected in the liquid.

The sensors or individual electrodes are often coated by spotting molecules onto the sensors. As the structure size of the sensors and electrodes decreases, however, this becomes more and more complicated. In the case of electrode sizes in the nanometers range, a coating can no longer be effected by spotting. Expensive and complicated methods such as photolithography, for example, are used to apply molecules specifically to the electrodes. A precise alignment of the equipment during coating is necessary and makes the method for producing the sensor arrays susceptible to faults and expensive.

SUMMARY

Described below is a device which is simpler and less expensive to produce in comparison with the related art. In particular, it is a device in which complicated alignment during the process of linking the molecules for detecting the chemical or biochemical substances with the sensors is obviated. Also described are a method for producing the device and the use of the device in which, without complicated alignment, with the aid of molecules specifically binding to the substances to be detected, the sensors can be directly or indirectly linked with the molecules, e.g., via the liquid and, during detection, sensors can specifically detect the substances electrochemically.

Advantageous configurations of the device, of the method and of the use of the device emerge from the dependent subclaims. In this case, the features of the alternative independent claims can be combined with features of one respectively assigned subclaim or with features of a plurality of assigned subclaims.

The device for detecting chemical or biochemical substances in liquids has a first and a second carrier. A surface of the first carrier includes a sensor array having a plurality of electrochemical sensors. The second carrier has a porous layer having at least one functional region in which specifically binding catcher molecules are immobilized. The at least one functional region is arranged directly adjacent to at least one non-functionalized region. The surface of the first carrier and the porous layer of the second carrier are in contact with one another directly or indirectly via a liquid and/or gaseous medium. In each case a plurality of sensors of the sensor array are assigned to the at least one functional region and the at least one non-functionalized region.

As a result of the arrangement of the sensors in array form on the first carrier and as a result of the assignment of in each case a plurality of sensors to at least one functional region and to at least one non-functionalized region of the second carrier, a distinction can be drawn between different regions in a spatially resolved manner during an electrochemical measurement. A precise alignment of the first carrier with respect to the second carrier during the linking process can be obviated.

Upon introduction of the liquid including substances to be detected into the second carrier and an electrochemical measurement with the aid of the sensors of the sensor array, the sensors which are in contact with a functional region yield an increased measurement signal. The latter is caused by the interaction of the substances to be detected with the catcher molecules. Sensors which are in contact with non-functionalized regions yield no signal or only a small signal typical of the background reactions.

The more sensors are assigned to the respective regions, the more precisely the spatial resolution of the regions and assignment of the chemical or biochemical reactions to regions can be effected. The resolution is analogous to the resolution of an optical camera. With a higher optically active number of pixels of an optical camera, a higher resolution of a recorded optical image is achieved. Precise alignment of the camera with the object to be recorded is not necessary. The brightness and/or color values of the pixels of the recorded image produce, in the overall consideration, contours of the object with which the latter can be unambiguously identified within the image. After identification of the object, that is to say differentiation from the background, its properties can be evaluated more precisely.

The device functions analogously to an optical camera and thus, can be designated as an electrochemical camera. A plurality of sensors are assigned to a respective region. Chemical or biochemical reactions in the respective region are measured and imaged by a plurality of sensors. The greatly different reactions in a functional region in comparison with a non-functionalized region lead to signals at sensors assigned to the functional region which are different than signals, measured at sensors, assigned to a non-functionalized region. As a result of the arrangement of the sensors in array form and the associated knowledge of their spatial position on the first carrier, it is possible to distinguish between the position of different regions as a result of the assignment of the sensors to the regions. The spatial arrangement of the sensors on the first carrier enable the device to determine the spatial position of the regions in the porous layer of the second carrier.

The porous layer of the second carrier of the device may have at least two different functional regions which are spatially at a distance from one another. In this case, at least one region differs from at least one further region with regard to its catcher molecules. This enables different chemical or biochemical substances to be detected.

A particularly simple construction of the device and a good assignment of the sensors to the regions result if each sensor of the sensor array has an active area, which is arranged in a first plane, and surfaces of the at least two functional regions form a second plane, which is arranged such that it lies opposite the first plane. In each case the surface of a functional region in the second plane can be larger than the sum of the active areas of sensors which are in each case assigned to the functional region in the first plane. Even without precise alignment, as a result of this construction of the device, the assignment of a plurality of sensors to a respective region is automatically provided when the first carrier is brought into contact with the second carrier.

The catcher molecules can be immobilized in a manner spatially distributed three-dimensionally in the porous material. As a result, a particularly large number of catcher molecules are arranged in a very confined space in the porous material and the large number of catcher molecules can bind a large amount of substance to be detected. As a result, the signal-to-noise ratio during the electrochemical measurement becomes high and a large difference between signals from functional regions and non-functionalized regions is obtained.

In accordance with the concept of an electrochemical camera, the sensors can be arranged in the form of a pixel array regularly on the surface of the first carrier. This makes it possible to evaluate the spatial assignment of measurement signals more simply.

A particularly large amount of active area of the sensors can be arranged on a surface having a specific area if the individual sensors have a rectangular, e.g., square, circumference. A good signal/noise ratio and relatively large measurement signals are obtained as a result of the relatively large active area of the sensors.

A simple spatial assignment of the sensors to the regions is obtained if spaced-apart functional regions are arranged in the form of an array in and/or on the porous layer, with a number m of different functional regions at substantially the same spatial distance respectively from one another. The sensor array may have n sensors assigned to functional regions, with the number n of the assigned sensors with respect to functional regions is x times the number m of the functional regions, where x is greater than or equal to two. The regular arrangement of the functional regions and the assignment of the sensors of the sensor array to facilitate the evaluation of the measurement results and interpretation of the image arising from the measurement results. As a result, with low complexity, from the signals of the sensors and the knowledge of their position and also the knowledge of the distance between the functional regions, a spatially resolved image of the chemical or biochemical reactions in the second carrier can be obtained and reactions can be assigned to the measurement signals and/or regions.

Expedient embodiments of the device, which are easy to produce, are provided if a number m of functional regions is 8 and the number n of sensors is 32, and 4 sensors are assigned to each functional region, or if the number m of functional regions is 24 and the number n of sensors is 384, and 16 sensors are assigned to each functional region, or if the number m of functional regions is between 8 and 24 and the number n of sensors is between 32 and 384.

The sensors can be constructed from interdigital electrodes. Uncoated gold may be used as electrode material. Given this construction, a large number of chemical and biochemical reaction products can be measured electrochemically with a large signal composed of current or voltage. In this case, gold as electrode material is also stable over a long time.

The porous layer may have the form of a sheet (planar form), in particular the form of a paper strip. The porous layer can be embodied with a thickness of 100 micrometers, for example, and have an area of a few square millimeters. The functional regions can be embodied in the form of strips or bars, in particular parallelepipedal bars, which are delimited by two substantially parallel sectional areas spaced apart from one another along cross-sectional axes of the porous layer through the porous layer. In this case, the strips or bars of the functional regions may be arranged perpendicularly to a longitudinal axis of the porous layer, in particular of the paper strip. This results in a construction of the second carrier analogous to that of a test strip such as is used e.g. in glucose or pregnancy tests.

The porous layer may be constructed from a membrane or include a membrane, in particular composed of cellulose, nitrocellulose, lateral flow paper or a fabric. These materials are able to bind catcher molecules and to absorb liquids by capillary forces and transport them through the material. As a result, no devices for transporting the liquid, such as, e.g., pumps, are required for the functioning of the device.

Of course, the aforementioned devices can additionally be used in order to achieve faster or more uniform liquid transport.

The catcher molecules used can be, inter alia, antibodies or antigens, aptamers, DNA fragments, RNA fragments, or peptides or combinations of these molecules. The selection of the catcher molecules is dependent on the chemical or biochemical substances to be detected by the device.

In method for producing the device described below, a first carrier includes a sensor array constructed from a plurality of electrochemical sensors, and a second carrier is applied. The second carrier includes at least one functional region in or on a porous layer, in which specifically binding catcher molecules are immobilized. The at least one functional region is arranged directly adjacent to at least one non-functionalized region in or on the porous layer. As a result of the application, in each case a plurality of sensors of the sensor array are assigned to the at least one functional region and the at least one non-functionalized region.

It is advantageous in this case that the first carrier with the sensor array can be reused. The second carrier can be used as a disposable article and be replaced after each use of the device. Different tests with differently functionalized second carriers can be carried out using one and the same first carrier. Tests with e.g. samples from different patients can also be carried out using one and the same first carrier. Here the second carriers are replaced in each case after an examination of a patient's sample. If necessary, the first carrier can be cleaned and disinfected between two examinations, since in particular gold and silicon oxide surfaces of the first carrier and of the sensor array are very insensitive to cleaning agents and disinfectants and to agents that break down DNA, RNA and protein. They are not destroyed thereby in contrast to organic coatings. The organic catcher molecules, which in the related art are applied directly as a coating on the sensors, are contained in the porous second carrier in the method described below, and are not damaged during cleaning of the first carrier.

The method described below is particularly advantageous when the method is performed in temporally successive operations. The at least one functional region is introduced into the porous layer by dispensing, printing and/or spotting first. In a second operation temporally succeeding the first, the porous layer is directly or indirectly linked to the sensor array of the first carrier. This can be done in particular by the second carrier being placed onto the first carrier. Upon liquid being introduced into the porous layer, the at least one functional region and the at least one non-functionalized region in each case with the plurality of assigned sensors are linked to one another via the liquid. In this case, linked means that molecules such as e.g. reaction products of chemical or biochemical reactions which indicate the binding of the substances to be examined to the catcher molecules can pass to the electrochemical sensors (e.g. by diffusion or electric fields in the case of charged molecules). At the electrochemical sensors, the molecules e.g. of the reaction products are then detected electrochemically. As a result, directly or in the case of reaction products indirectly, detection of the chemical or biochemical substances in the liquid to be examined is effected in the case where the substances were bounded by the catcher molecules.

In a use of the device described below, a liquid including substances to be detected is applied to a second carrier, which includes a porous layer having at least one functional region in which specifically binding catcher molecules for binding to the substances to be detected are immobilized. The at least one functional region is arranged directly adjacent to at least one non-functionalized region in the porous layer. The liquid is transported at least partly through the porous layer in particular by capillary forces, wherein the substances to be detected specifically bind to the catcher molecules. The bound substances are directly or indirectly electrochemically detected with the aid of sensors of a sensor array on a second carrier which are assigned to the at least one functional region. In this case, the sensors of the sensor array on the second carrier which are assigned to the at least one non-functionalized region detect electrochemically that no substances to be detected were bound in the non-functionalized region.

The abovementioned advantages associated with the device arise for the method for producing the device and the use of the device.

BRIEF DESCRIPTION OF THE DRAWINGS

These and other aspects and advantages will become more apparent and more readily appreciated from the following description of the exemplary embodiments, taken in conjunction with the accompanying drawings of which:

FIG. 6 shows a sectional illustration of the device with enlarged depiction of a sensor with interdigital electrodes, and a schematic illustration of the detection reaction in a functional region.

DETAILED DESCRIPTION OF THE PREFERRED EMBODIMENT

Figure 1:
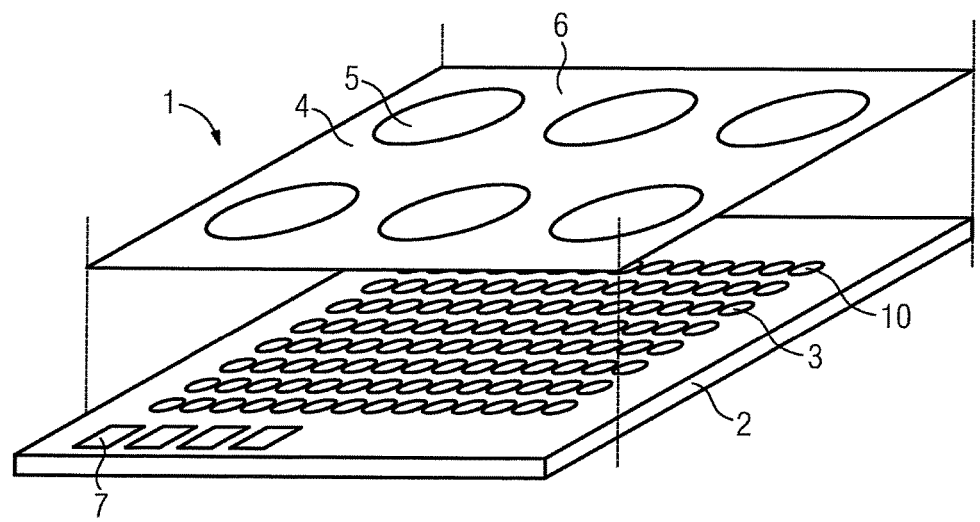
FIG. 1 schematically shows an oblique view of an exploded drawing of the device with a first and a second carrier, and FIG. 2 schematically shows a plan view of the second carrier with circular functional regions, wherein the first carrier situated underneath with sensor array is depicted as a view through the second carrier, and FIG. 3 schematically shows a plan view of the second carrier analogously to FIG. 2, but with strip- or bar-shaped functional regions, and FIG. 4 schematically shows a sectional illustration through the device in accordance with FIG. 3, and FIG. 5 schematically shows a sectional illustration of the device shortly before the second carrier is linked to the first carrier.

Reference will now be made in detail to the preferred embodiments, examples of which are illustrated in the accompanying drawings, wherein like reference numerals refer to like elements throughout.

FIG. 1 shows the device 1 with a first carrier 2, on the surface of which a sensor array 3 having electrochemical sensors 10 is formed. The electrochemical sensors 10 are formed in circular fashion and are arranged regularly, at equal distances from one another on the surface of the first carrier 2.

Electrical links, which are not illustrated for the sake of simplicity, to electrical connections 7 are formed on and/or in the first carrier 2. The electrical connections 7 enable the first carrier 2 to be electrically linked to a voltage supply and control/read-out and/or data processing unit (not illustrated). The electrochemical sensors 10 can be driven and read individually or in parallel via the connections 7 and the electrical links. Measurement signals, such as e.g. current-voltage values of the sensors 10, can be processed externally in the read-out and data processing unit. Alternatively, integrated circuits can also be formed on or in the first carrier, which process electrochemical signals and output the results as electrical signals via the contacts 7 to an external display unit (not illustrated).

In accordance with FIG. 1, a porous layer 4 of a second carrier is situated above the surface of the first carrier 2 with sensor array 3. In the porous layer 4, functional regions 5 are formed in array form at equal distances from one another, capture molecules 8 (cf. FIG. 6) being immobilized in the regions. The functional regions 5 are separated from one another by a non-functionalized region 6. The functional regions 5 illustrated in FIG. 1 are embodied in circular fashion, in a flat, sheet-type layer 4. In this context, sheet-type means that the form is analogous to that of a sheet of paper. The extent of the material of the porous layer 4 in a plane is considerably greater than in the perpendicular to the plane. Consequently, the circular functional regions 5 illustrated in FIG. 1 constitute cylindrical regions which, however, have a lateral surface that is almost negligible relative to their base area.

The base areas of the functional regions 5, which are arranged opposite the plane of the sensors 10, lie in one plane. This plane, called the plane of the functional regions hereinafter, is parallel to the plane of the sensors 10 of the sensor array. The surface area (or base area) of a functional region 5 in the plane of the functional regions is larger than the active area of a sensor 10. In this case, active area of a sensor 10 denotes the area which is in contact with liquid during the electrochemical measurement and therefore participates actively in the measurement by virtue of the fact that chemical reactions can take place at it or charges can pass through it.

When the device 1 is in use, the porous layer 4 of the second carrier lies directly on the first carrier 2 and thus on the sensor array 3. The contacts 7 are spaced apart from the porous layer 4 in order that they do not come into contact with liquid and do not cause any electrical short circuit during the use of the device. It can also be arranged on the rear side of the first carrier 2. The dashed lines in FIG. 1 represent the spatial assignment of the porous layer of the second carrier 4 relative to the first carrier 2 when the second carrier 4 is placed onto the first carrier 2.

Figure 2:
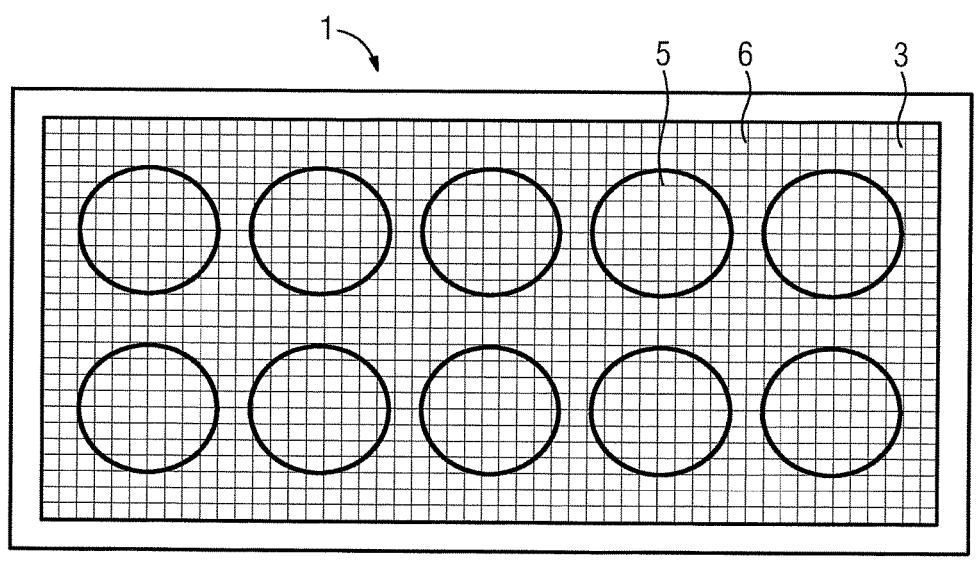

FIG. 2 schematically illustrates a plan view of the device 1 as depicted in FIG. 1. In this case, the contacts 7 are not shown, for the sake of simplicity. The illustration represents a situation in which the porous layer 4 of the second carrier is in direct contact with the first carrier 2. The second carrier 4, with circular functional regions 5, is illustrated in a transparent fashion, in order that the first carrier 2 with sensor array 3 situated underneath can be illustrated as a view through the second carrier 4. Generally, the second carrier 4 is not embodied in an optically transparent fashion.

The sensors 10 illustrated in FIG. 2 are square, arranged at a small distance from one another, in which case they form a pixel array, analogous to that of an optical camera chip for recording optical images. The sensor array 3 is in contact with the porous layer 4 of the second carrier, wherein the pores of the porous layer are filled with air in the basic state. When the device is filled with the liquid to be examined, the liquid is drawn, e.g. by capillary forces, into the pores which are interconnected. After complete filling, the sensors 10 of the sensor array 3 are in contact with the porous layer 4 of the second carrier directly, or indirectly via the liquid.

The functional regions 5 in FIG. 2 are embodied in circular fashion in the plan view and are arranged at an identical row distance from one another, in array form in the porous layer 4. In the functional regions 5, catcher molecules are immobilized, i.e. bound to the porous material in a uniformly distributed manner. Possible bonds can be effected e.g. by coulomb interactions, covalent bonds or by the restriction of the mobility of large molecules in small pores. The functional regions 5 are completely enclosed by a non-functionalized region 6, which is embodied in a continuous fashion, in the porous layer 4 as viewed along the plane of the functional regions. Perpendicular to the plane of the functional regions, the functional regions 5 are embodied in a manner extending completely through the porous layer 4.

When the second carrier 4 is placed onto the first carrier 2, sensors 10 are assigned to the functional regions 5. In the plan view in FIG. 2, assigned means that they lie within the circular functional regions 5. Analogously, when the second carrier 4 is placed onto the first carrier 2, sensors 10 are assigned to the non-functionalized region 6. They lie within the non-functionalized region 6 in FIG. 2, and outside the circular functional regions 5.

If the device in FIG. 2 is filled with liquid containing substances 9 to be detected, then the substances bind to catcher molecules 8, (cf. FIG. 6) specifically in the functional regions 5, in which the specifically binding catcher molecules 8 for the substances 9 are immobilized. In an electrochemical measurement, sensors 10 assigned to these regions produce signals indicating the specific binding of the substances 9 to be detected. Sensors 10 assigned to the non-functionalized region 6 measure only background reactions such as e.g. the formation and charge reversal of double layers. Functional regions 5 in which no substances 9 to be detected have bound likewise measure only background reactions. Errors such as arise e.g. as a result of diffusion and movement in the electric field of reaction products during the detection of the specifically bound substances 9 shall be discarded in this consideration.

If the sensors 10 assigned to a functional region 5 measure large signals, e.g. large currents in the case of amperometric measurements, directly or indirectly as a result of the binding of a substance 9 to be detected to the specific catcher molecules 8 immobilized in the functional region 5, then sensors 10 in the non-functionalized region 6 can measure small signals, e.g. small currents. Sensors 10 lying on the circumference of the circular functional region 5 measure signals or currents which are between the signals or currents of the sensors 10 of the functional regions 5 and signals or currents of the sensors 10 of the non-functionalized regions 6. In this case, the signal or current magnitude can be a measure of the common area between sensor 10 and functional region 5.

Precise alignment of the second carrier 4 upon being applied on or brought into contact with the first carrier 2 can be obviated. On account of the arrangement of the sensors 10 in array form and an assignment of more than one sensor 10 respectively to a functional region 5 and a non-functionalized region 6, the position of the regions relative to the sensors should be differentiated during an electrochemical measurement on the basis of the signals. Additionally introduced substances in the functionalized regions 5 which are electrochemically active, but do not impede or prevent the electrochemical detection of the binding of the substances 9 to be detected in the liquid, can further improve differentiation. Thus, functional regions 5 in which no substances from the liquid bind, since these substances to be detected are not contained in the liquid (negative test), can also be differentiated from the non-functionalized region 6.

The sensors 10 are arranged in array form at regular distances from one another, wherein the distances should be made as small as possible, but have a value which minimizes cross talk as a problem during the electrochemical measurement. The more sensors 10 are arranged at a small distance on the surface, the higher the spatial electrochemical resolution (analogous to the optical resolution in cameras) and differentiation of the functional regions 5 become. Typical values for the distance of the sensors are in the range of micrometers, in particular 100 to 1000 micrometers. For a higher resolution, the distances can also be embodied in the range of nanometers. In examinations which do not require a high spatial resolution, distances in the millimeters through to the centimeters range are also possible.

As a result of the arrangement of the sensors 10 in array form with a small distance and functional regions 5 and also non-functionalized regions 6 which are significantly larger than the active area of a sensor 10, when the second carrier 4 is placed onto the first carrier 2 it is ensured that a plurality of sensors 10 are assigned to each functional region 5 and also to each non-functionalized region 6, that is to say that, in the plan view of FIG. 2, in each case a plurality of sensors 10 lie below a respective region 5, 6. It is thus ensured, independently of the exact position of the first carrier 2 relative to the second carrier 4, that sensors 10 yield a measurement signal during an electrochemical measurement for each region 5, 6. The magnitude of the measurement signal reveals in the evaluation which sensor 10 is assigned to which region 5, 6. In the totality of the sensors 10, given knowledge of the spatial arrangement thereof, an electrochemical image of the second carrier 4 arises, analogously to an optical image during the imaging of objects with the aid of an optical CCD camera.

On the basis of the resultant contours or the position of the sensors 10, between which greatly differing signals are measured, regions 5, 6 can be differentiated from one another or demarcated from one another and spatially assigned, and regions 5, 6 can be identified on the basis of the magnitude of the signals. The magnitude of the signal is analogous to the gray-scale value in an optical black/white image. Objects can be differentiated from their background by large differences in adjacent values, which represent contours, and can be identified on the basis of the structure or distribution of the values within a contour (reveals e.g. a face or a house . . . in an image) and the form of the contour. The same applies analogously to the electrochemical measurement values of the sensors 10 of the sensor array 3, which produce an electrochemical image of the second carrier 4.

Figure 3:
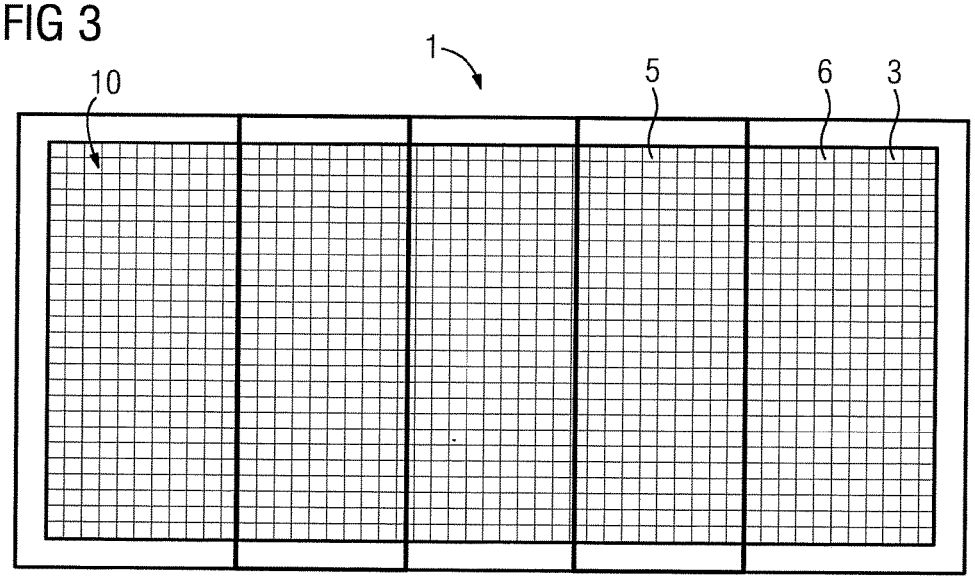

FIG. 3 shows a device with a first carrier 2 and a porous layer of the second carrier 4, which, in contrast to the device in FIG. 2 has functional regions in bar form or strip form instead of circular form or cylindrical form. The carrier 4 in FIG. 3 has a longitudinal axis from the left-hand to the right-hand side of FIG. 3. Perpendicular to the longitudinal axis in the plane of the drawing, the carrier 4 has a transverse axis. Transverse axes of the carrier 4 or of the porous layer of the carrier 4 are identical to longitudinal axes of the bar form or strip form of the functional regions 5. The functional regions 5 illustrated in FIG. 3 are formed completely continuously through the porous layer both along their longitudinal axis and along their height. Alternatively, they can also be formed only partly along their longitudinal axis and/or along their height in or on the porous material. In this case, height of the functional regions 5 denotes the extent along an axis formed perpendicular to the longitudinal axis and transverse axis of the carrier 4.

Figure 4:
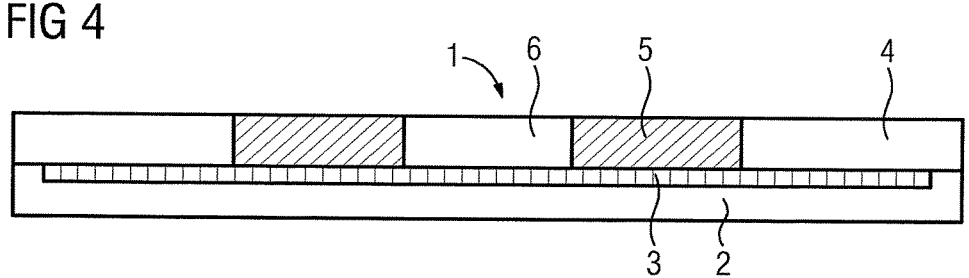

FIG. 4 shows a cross section along a longitudinal axis of the device illustrated in FIG. 3. The functional regions 5 and the non-functionalized regions 6, which are formed in the porous layer of the second carrier 4, are in direct contact with the sensor array 3, which is formed on the front side of the first carrier 2. The functional regions 5 formed in a manner extending through the porous layer 4 separate the non-functionalized region 6 into a plurality of non-functionalized regions 6 that are spatially completely separated and spaced apart from one another. Functional and non-functionalized regions 5 and 6, respectively, are arranged alternately in the porous layer 4 along the longitudinal axis thereof. The bar-shaped functional regions 5 produce parallelepipeds, in the volume of which the catcher molecules 8 (cf. FIG. 6) are immobilized in a uniformly distributed manner. Different catcher molecules 8 can be arranged in different functional regions 5, as a result of which different functional regions 5 serve for detecting different substances 9 from the liquid including substances to be detected.

Figure 5:
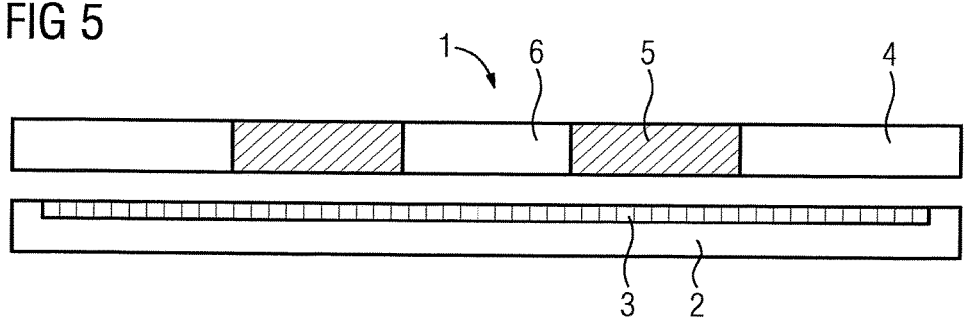

FIG. 5 illustrates the device from FIG. 4, in the state before or after the first carrier 2 was brought into contact with the second carrier 4. The first carrier 2 can be reused, the second carrier being replaced as a disposable carrier. Thus, costs can be saved e.g. when examining patient samples from different patients. Between two uses of the carrier 2, the latter can be cleaned or disinfected.

FIG. 6 schematically shows the device illustrated in FIG. 4 in operation. A drop of liquid to be examined, including substances 9 to be detected is passed to the porous layer 4. On account of capillary forces, the liquid to be examined is absorbed by the porous layer 4, such that the porous layer 4 is largely or completely filled or impregnated with liquid to be examined. In functional regions 5, the substances 9 to be detected bind specifically to the immobilized catcher molecules 8.

Afterward, the porous layer 4 is purged using e.g. ultra pure or buffer solution. Non-bound substances and liquid to be examined are thus removed from the porous layer 4. The bound substances 9 to be detected can be directly electrochemically detected, as is indicated schematically in FIG. 6. Alternatively, marker molecules dissolved in a liquid can be passed into the porous layer 4, which bind to the specifically bound substances to be detected specifically, i.e. only to substances to be detected. The marker molecules are then detected electrochemically directly or indirectly e.g. by redox cycling.

The marker molecules can be provided with labels, e.g. with enzyme labels bound to the marker molecules. During an electrochemical detection, substrate molecules are converted e.g. at the enzyme labels, in particular from a starting material to a product. At the active sensor surface or the electrode, the converted substrate molecules (product) are oxidized or reduced, wherein it is possible to measure a charge transfer via the electrode or a change in the charge near the electrode (in particular a current or a change in the voltage). If a sensor is constructed from at least two electrodes of opposite polarity (positive+/negative−), then the product can be oxidized to form an oxidized product (Ox) at one electrode (+), and the oxidized product can be reduced again to (Red) at the other electrode (−).

The quantity of charge converted at the electrodes can be measured in a time-dependent manner and is a measure of the conversion of starting material to product at the enzyme label and thus of the specific binding of substance 9 to be detected to catcher modules 8. It is only when the substance molecule 9 that is to be detected and is specific to the catcher molecule is present in the liquid to be analyzed at a time-dependent charge conversion takes place at the assigned sensor and is measured.

As is illustrated as an enlarged view in FIG. 6, the sensor 10 for detecting the bound substances 9 to be detected includes electrochemical electrodes, which can be embodied e.g. as interdigital electrodes. The interdigital electrodes can be embodied in a comb-like manner, with a distance of e.g. one micrometer between adjacent webs of two electrodes and a width of the webs of in each case e.g. one micrometer. A sensor 10 can be formed of two intermeshing comb-like interdigital electrodes, wherein the sensor 10 has a diameter of e.g. 150 micrometers.

Finger-shaped gold electrodes are particularly inert chemically in liquids and well suited as working electrodes for electrochemical current and/or voltage measurements. Inter alia, amperometry, voltametry, coulometry or impedance spectroscopy are employed as measurement methods. Reference electrodes and counterelectrodes used can likewise be gold electrodes or electrodes composed of materials such as e.g. platinum, silver or silver/silver chloride.

The electrodes of the sensors 10 can easily be produced photolithographically by standard processes in semiconductor technology. Silicon is well suited as material for the first carrier 2, but other materials such as e.g. germanium, gallium arsenide and other semiconductors and also insulator materials such as plastic, epoxy resin or printed circuit boards are also suitable. The first carrier 2 can be embodied as a chip as illustrated in FIG. 2, wherein electronic circuits for processing the measured current-voltage signals can be integrated below the electrodes or in a separate region of the chip. Methods that are customary in semiconductor technology in the production of the first carrier 2 with the sensors 10, insulations (e.g. silicon dioxide or photoresistance), integrated circuits and contacts make it possible to produce the first carrier 2 with low costs.

Commercially available test strips such as are obtainable e.g. for pregnancy tests, glucose tests and urine and blood tests, can serve as the second carrier 4. The porous layer of the second carrier 4 can be produced, inter alia, from nitrocellulose, paper or fabric or can contain these materials.

The device can be used in a flow cell or can be integrated in a housing. Particularly cost-effective housings can be produced from plastic. Cooling and/or heating devices can be provided in order to control reactions by way of the temperature.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide* v. *DIRECTV*, 358 F3d 870, 69 USPQ2d 1865 (Fed. Cir. 2004).

The invention claimed is:

1. A device for detecting chemical or biochemical substances in liquids, comprising:
    a first carrier including a plurality of electrochemical sensors forming a sensor array on a surface, wherein the plurality of electrochemical sensors of the sensor array each have respective active areas, the active areas being arranged in a first plane,
        wherein the plurality of electrochemical sensors are assigned to at least one functional region and at least one non-functional region, and
        wherein the assigned electrochemical sensors lie within respective surfaces of each of a plurality of functional regions; and
    a second carrier forming a second plane disposed opposite of, and in direct contact with, the first plane comprising; a single continuous porous layer made of a porous material forming a plurality of non-functionalized regions and a plurality of functional regions arranged in substantially identical distances from each other, in which specifically binding catcher molecules are immobilized and spatially distributed three-dimensionally in the porous layer,
        wherein the plurality of functional regions are arranged directly or indirectly adjacent to one of said plurality of non-functionalized regions, each of the plurality of functional regions and the plurality of non-functionalized regions being positioned in direct sensing with a corresponding group of the plurality of electrochemical sensors in the sensor array,
        wherein each of the plurality of functional regions have; (i) a respective surface in the second plane that is larger in area than a sum of the respective active areas of the plurality of electrochemical sensors in the first plane, and (ii) at least four electrochemical sensors assigned to each of the plurality of functional regions, and
        wherein the functional regions are arranged perpendicular to a longitudinal axis of the porous layer and extend through the entire thickness of the porous layer, such that a precise alignment of the first carrier with respect to the second carrier during the linking of molecules for detecting chemical or biochemical substances with the plurality of electrochemical sensors is obviated.

2. The device as claimed in claim 1, wherein the plurality of functional regions differ in regard to the catcher molecules specifically bound thereto.

3. The device as claimed in claim 1, wherein the plurality of electrochemical sensors have a square form and/or are arranged in a pixel array regularly on the surface of the first carrier.

4. A device for detecting chemical or biochemical substances in liquids, comprising:
    a first carrier including a plurality of electrochemical sensors forming a sensor array on a surface, wherein the plurality of electrochemical sensors of the sensor array each have respective active areas, the active areas being arranged in a first plane,
        wherein the plurality of electrochemical sensors are assigned to at least one functional region and at least one non-functional region, and
        wherein the assigned electrochemical sensors lie within respective surfaces of each of a plurality of functional regions; and
    a second carrier forming a second plane disposed opposite of, and in direct contact with, the first plane comprising; a single continuous porous layer made of a porous material forming a plurality of non-functionalized regions and a plurality of functional regions arranged with a number of different functional regions, in which specifically binding catcher molecules are immobilized and spatially distributed three-dimensionally in the porous layer,
        wherein the plurality of functional regions are arranged directly or indirectly adjacent to one of said plurality of non-functionalized regions, each of the plurality of functional regions and the plurality of non-functionalized regions being positioned in direct sensing with a corresponding group of the plurality of electrochemical sensors in the sensor array,
        wherein each of the plurality of functional regions have; (i) a respective surface in the second plane that is larger in area than a sum of the respective active areas of the plurality of electrochemical sensors in the first plane, and (ii) at least four electrochemical sensors assigned to each of the plurality of functional regions, and
        wherein the functional regions are arranged perpendicular to a longitudinal axis of the porous layer and extend through the entire thickness of the porous layer, such that a precise alignment of the first carrier with respect to the second carrier during the linking of molecules for detecting chemical or biochemical substances with the plurality of electrochemical sensors is obviated.

5. The device of claim 4, wherein the sensor array has a number of electrochemical sensors positioned in sensing relationship to each of the functional regions, the number of electrochemical sensors in sensing relationship to each of the functional regions being at least twice the number of different function regions.

6. The device as claimed in claim 5, wherein the number of the functional regions is between 8 and 24, to each inclusive of 8 and 24, and the number of electrochemical sensors in sensing relationship is between of the functional regions is between 32 and 384, inclusive of 32 and 384.

7. The device as claimed in claim 6, wherein the number of the functional regions is eight and the number of electrochemical sensors in sensing relationship to each of the functional regions is 32.

8. The device as claimed in claim 6, wherein the number of the functional regions is 24 and the number of electrochemical sensors in sensing relationship to each of the functional regions is 384, and sixteen sensors are assigned to each functional region.

9. The device as claimed in claim 1, wherein the plurality of functional regions are embodied as parallelepipedal bars.

10. The device as claimed in claim 1, wherein the plurality of electrochemical sensors are constructed of electrodes selected from the group consisting at least one of interdigital electrodes and uncoated gold electrodes.

11. The device as claimed in claim 10, wherein the porous layer of the second carrier comprises a membrane composed of a material selected from the group consisting of at least one of cellulose, nitrocellulose, lateral flow paper and a fabric.

12. The device as claimed in claim 11, wherein the porous layer is formed as a sheet.

13. The device as claimed in claim 12, wherein the porous layer is formed as a paper strip.

14. The device as claimed in claim 11, wherein the catcher molecules selected from the group consisting of at least one of antibodies, antigens, aptamers, DNA fragments, RNA fragments and peptides.

15. The device as claimed in claim 1, wherein between four and sixteen electrochemical sensors are assigned to each functional region and lie within respective surfaces of the functional regions.

16. The device as claimed in claim 1, wherein the functional regions are embodied in the form of strips or bars arranged perpendicularly to a longitudinal axis of the porous layer and through the entire thickness of the porous layer.

17. The device as claimed in claim 1, wherein the first carrier is embodied as a chip.

18. The device as claimed in claim 1, wherein the device comprises a cooling device in order to control reactions made by way of the temperature.

19. The device as claimed in claim 1, wherein the device comprises a heating device in order to control reactions made by way of the temperature.

* * * * *